US007641691B2

(12) United States Patent
Lotz et al.

(10) Patent No.: US 7,641,691 B2
(45) Date of Patent: Jan. 5, 2010

(54) BIODEGRADABLE/BIOACTIVE NUCLEUS PULPOSUS IMPLANT AND METHOD FOR TREATING DEGENERATED INTERVERTEBRAL DISCS

(75) Inventors: Jeffrey C. Lotz, San Mateo, CA (US); Olivier K. Colliou, Los Gatos, CA (US); David S. Bradford, Sausalito, CA (US)

(73) Assignee: The Regents of the University of California, Oakland, CA (US)

(*) Notice: Subject to any disclaimer, the term of this patent is extended or adjusted under 35 U.S.C. 154(b) by 81 days.

(21) Appl. No.: 11/505,783

(22) Filed: Aug. 16, 2006

(65) Prior Publication Data

US 2006/0293751 A1    Dec. 28, 2006

Related U.S. Application Data

(62) Division of application No. 10/154,857, filed on May 24, 2002, now Pat. No. 7,156,877.

(60) Provisional application No. 60/301,882, filed on Jun. 29, 2001.

(51) Int. Cl.
*A61F 2/44* (2006.01)
(52) U.S. Cl. .................................................. 623/17.12
(58) Field of Classification Search ... 623/17.11–17.16, 623/23.51, 23.54, 23.61, 23.63, 23.64, 23.67, 623/23.68, 908; 606/61, 99
See application file for complete search history.

(56) References Cited

U.S. PATENT DOCUMENTS 3,867,728 A    2/1975    Stubstad et al.
3,875,595 A    4/1975    Froning
4,309,777 A    1/1982    Patil
4,341,218 A    7/1982    U
4,349,921 A    9/1982    Kuntz
4,364,392 A    12/1982   Strother et al.
4,517,979 A    5/1985    Pecenka
4,697,584 A    10/1987   Haynes
4,714,469 A    12/1987   Kenna
4,772,287 A    9/1988    Ray et al.
4,904,260 A    2/1990    Ray et al.
4,911,718 A    3/1990    Lee et al.
4,932,969 A    6/1990    Frey et al.
4,932,975 A    6/1990    Main et al.
4,944,749 A    7/1990    Becker (Continued)

FOREIGN PATENT DOCUMENTS

EP          0700671 A1    3/1996

(Continued)

*Primary Examiner*—Pedro Philogene
(74) *Attorney, Agent, or Firm*—John P. O'Banion

(57) ABSTRACT

A bioactive/biodegradable nucleus implant for repairing degenerated intervertebral discs that is inflated inside the nucleus space after the degenerated nucleus has been removed to re-pressurize the nuclear space within the intervertebral disc. The implant is inflated with a high molecular weight fluid, gel or combination of fluid and elastomer, preferably an under-hydrated HA hydrogel/growth factor mixture with or without host cells. The implant includes an internal, integral, self-sealing valve that allows one-way filling of the implant after it is placed within the disc, and is made from a material that allows fibrous in growth thereby stabilizing the implant. A variety of substances can be incorporated into the implant to promote healing, prevent infection, or arrest pain.

12 Claims, 19 Drawing Sheets

U.S. PATENT DOCUMENTS

| | | | |
|---|---|---|---|
| 5,047,055 | A | 9/1991 | Bao et al. |
| 5,084,061 | A | 1/1992 | Gau et al. |
| 5,108,404 | A | 4/1992 | Scholten et al. |
| 5,108,430 | A | 4/1992 | Ravo |
| 5,108,438 | A | 4/1992 | Stone |
| 5,141,508 | A | 8/1992 | Bark et al. |
| 5,144,708 | A | 9/1992 | Pekar |
| 5,171,280 | A * | 12/1992 | Baumgartner ............ 623/17.12 |
| 5,171,281 | A | 12/1992 | Parsons et al. |
| 5,181,921 | A * | 1/1993 | Makita et al. ................ 606/195 |
| 5,192,326 | A * | 3/1993 | Bao et al. ................. 623/17.12 |
| 5,219,360 | A | 6/1993 | Georgiade |
| 5,258,043 | A | 11/1993 | Stone |
| 5,314,478 | A | 5/1994 | Oka et al. |
| 5,458,643 | A | 10/1995 | Oka et al. |
| 5,496,370 | A | 3/1996 | Hamas |
| 5,522,899 | A | 6/1996 | Michelson |
| 5,534,028 | A | 7/1996 | Bao et al. |
| 5,534,030 | A | 7/1996 | Navarro et al. |
| 5,545,229 | A | 8/1996 | Parsons et al. |
| 5,549,679 | A | 8/1996 | Kuslich |
| 5,556,429 | A | 9/1996 | Felt |
| 5,562,736 | A | 10/1996 | Ray et al. |
| 5,571,189 | A | 11/1996 | Kuslich |
| 5,632,777 | A | 5/1997 | Petrick |
| 5,645,597 | A | 7/1997 | Krapiva |
| 5,674,295 | A | 10/1997 | Ray et al. |
| 5,674,296 | A | 10/1997 | Bryan et al. |
| 5,700,288 | A | 12/1997 | Eaton |
| 5,702,454 | A | 12/1997 | Baumgartner |
| 5,716,416 | A * | 2/1998 | Lin ......................... 623/17.16 |
| 5,755,797 | A | 5/1998 | Baumgartner |
| 5,779,672 | A | 7/1998 | Dormandy, Jr. |
| 5,795,353 | A | 8/1998 | Felt |
| 5,800,549 | A | 9/1998 | Bao et al. |
| 5,823,852 | A | 10/1998 | Chu |
| 5,824,093 | A | 10/1998 | Ray et al. |
| 5,871,777 | A | 2/1999 | Ducheyne et al. |
| 5,888,220 | A | 3/1999 | Felt et al. |
| 5,919,235 | A | 7/1999 | Husson et al. |
| 5,964,807 | A | 10/1999 | Gan et al. |
| 5,976,186 | A | 11/1999 | Bao et al. |
| 5,980,504 | A | 11/1999 | Sharkey et al. |
| 6,022,376 | A | 2/2000 | Assell et al. |
| 6,079,868 | A | 6/2000 | Rydell |
| 6,093,205 | A | 7/2000 | McLeod et al. |
| 6,095,149 | A | 8/2000 | Sharkey et al. |
| 6,099,514 | A | 8/2000 | Sharkey et al. |
| 6,113,639 | A | 9/2000 | Ray et al. |
| 6,139,579 | A | 10/2000 | Steffee et al. |
| 6,140,452 | A | 10/2000 | Felt et al. |
| 6,149,688 | A | 11/2000 | Brosnahan et al. |
| 6,156,067 | A | 12/2000 | Bryan et al. |
| 6,162,252 | A | 12/2000 | Kuras et al. |
| 6,193,757 | B1 | 2/2001 | Foley et al. |
| 6,224,630 | B1 | 5/2001 | Bao et al. |
| 6,248,131 | B1 | 6/2001 | Felt et al. |
| 6,280,475 | B1 * | 8/2001 | Bao et al. ................. 623/17.16 |
| 6,306,177 | B1 | 10/2001 | Felt et al. |
| 6,375,682 | B1 | 4/2002 | Fleischmann et al. |
| 6,402,784 | B1 * | 6/2002 | Wardlaw .................. 623/17.11 |
| 6,443,988 | B2 | 9/2002 | Felt et al. |
| 6,565,606 | B1 | 5/2003 | Bruce et al. |
| 6,582,467 | B1 * | 6/2003 | Teitelbaum et al. ....... 623/17.11 |
| 6,805,715 | B2 | 10/2004 | Reuter et al. |
| 2001/0031974 | A1 * | 10/2001 | Hadlock et al. ............. 606/152 |
| 2001/0034526 | A1 | 10/2001 | Kuslich et al. |
| 2002/0068975 | A1 | 6/2002 | Teitelbaum et al. |
| 2002/0082638 | A1 | 6/2002 | Porter et al. |
| 2002/0147496 | A1 | 10/2002 | Belef et al. |
| 2002/0147497 | A1 | 10/2002 | Belef et al. |
| 2003/0199984 | A1 | 10/2003 | Trieu |
| 2003/0220649 | A1 | 11/2003 | Bao et al. |
| 2004/0024463 | A1 | 2/2004 | Thomas, Jr. et al. |
| 2004/0034427 | A1 | 2/2004 | Goel et al. |
| 2004/0073308 | A1 | 4/2004 | Kuslich et al. |

FOREIGN PATENT DOCUMENTS

| | | |
|---|---|---|
| EP | 0919209 A1 | 6/1999 |
| FR | 2639823 A1 | 12/1988 |
| GB | 2303555 A | 2/1997 |
| WO | 9108560 A1 | 6/1991 |
| WO | 9531946 A1 | 11/1995 |
| WO | 9720569 A2 | 12/1997 |
| WO | 9855053 A1 | 10/1998 |
| WO | 9902108 A1 | 1/1999 |
| WO | 9915211 A1 | 1/1999 |
| WO | 9904720 A1 | 4/1999 |
| WO | 9937395 A1 | 7/1999 |
| WO | 9947082 A1 | 9/1999 |
| WO | 9985863 A1 | 10/1999 |
| WO | 9961084 A1 | 12/1999 |
| WO | 9962439 A1 | 12/1999 |
| WO | 0002999 A2 | 1/2000 |
| WO | 0004851 A1 | 2/2000 |
| WO | 0025706 A1 | 5/2000 |
| WO | 0064385 A1 | 11/2000 |
| WO | 0128468 A1 | 4/2001 |
| WO | 0160268 A1 | 8/2001 |
| WO | 0217825 A2 | 3/2002 |

* cited by examiner

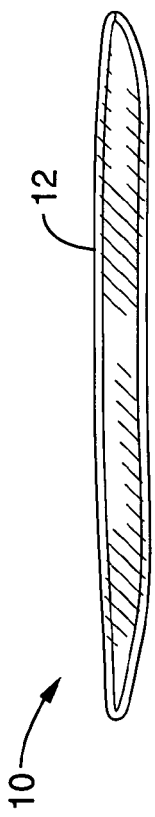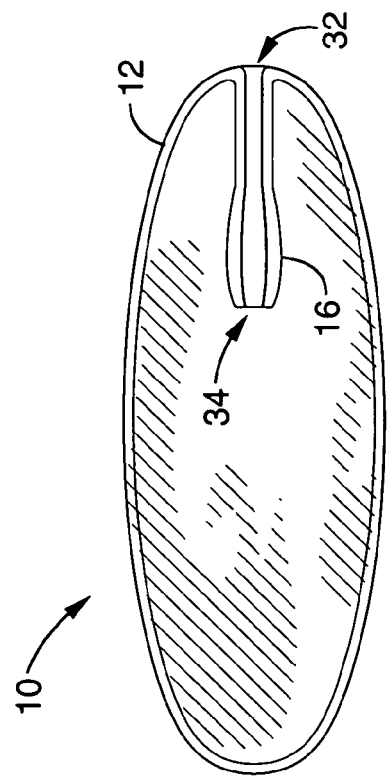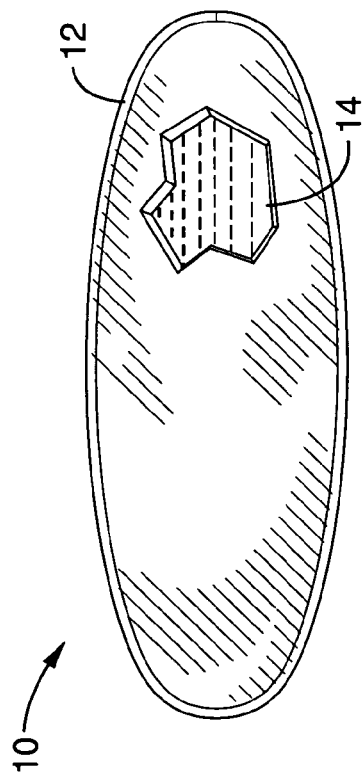

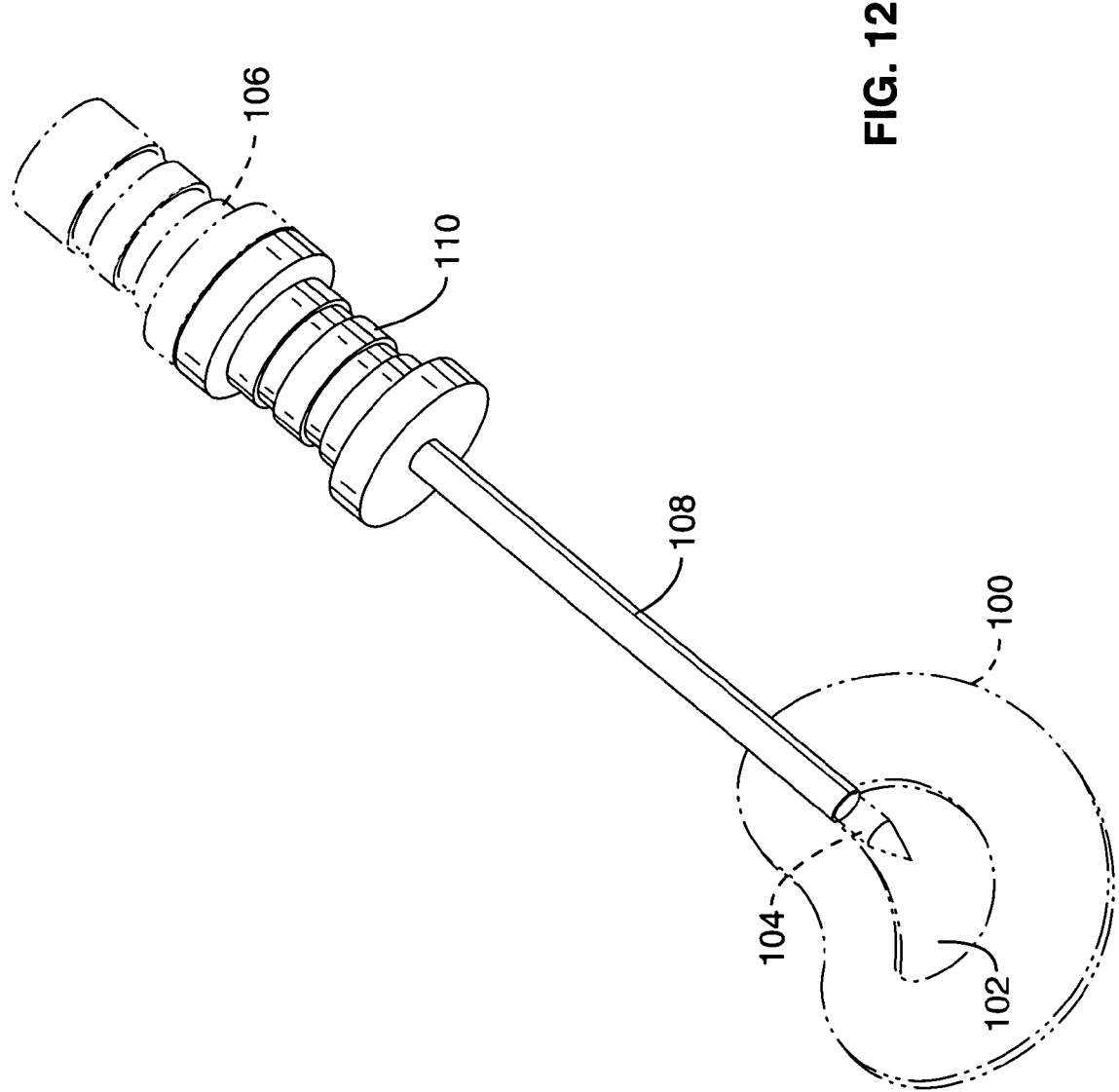

BIODEGRADABLE/BIOACTIVE NUCLEUS PULPOSUS IMPLANT AND METHOD FOR TREATING DEGENERATED INTERVERTEBRAL DISCS

CROSS-REFERENCE TO RELATED APPLICATIONS

This application is a divisional of application Ser. No. 10/154,857, filed on May 24, 2002, now U.S. Pat. No. 7,156,877, incorporated herein by reference in its entirety, which claims priority from U.S. provisional application Ser. No. 60/301,882, filed on Jun. 29, 2001, incorporated herein by reference in its entirety.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

The present invention pertains generally to repairing intervertebral disc disorders, and more particularly to an implant and surgical procedure for repairing a degenerated intervertebral disc.

2. Description of the Background Art

An estimated 4.1 million Americans annually report intervertebral disc disorders, with a significant portion of them adding to the nearly 5.2 million low-back disabled. Though the origin of low-back pain is varied, the intervertebral disc is thought to be a primary source in many cases, and is an initiating factor in others where a degenerated disc has led to altered spinal mechanics and non-physiologic stress in surrounding tissues.

The intervertebral disc is a complex structure consisting of three distinct parts: the nucleus pulposus; the annulus fibrosus; and the cartilaginous end-plates. The nucleus pulposus is a viscous, mucoprotein gel that is approximately centrally located within the disc. It consists of abundant sulfated glycosaxninoglycans in a loose network of type II collagen, with a water content that is highest at birth (approximately 80%) and decreases with age. The annulus fibrosus is that portion of the disc which becomes differentiated from the periphery of the nucleus and forms the outer boundary of the disc. The transition between the nucleus and the annulus is progressively more indefinite with age. The annulus is made up of coarse type I collagen fibers oriented obliquely and arranged in lamellae which attach the adjacent vertebral bodies. The fibers run the same direction within a given lamella but opposite to those in adjacent lamellae. The collagen content of the disc steadily increases from the center of the nucleus to the outer layers of the annulus, where collagen reaches 70% or more of the dry weight. Type I and II collagen are distributed radially in opposing concentration gradients. The cartilaginous end-plates cover the end surfaces of the vertebral bodies and serve as the cranial and caudal surfaces of the intervertebral disc. They are composed predominately of hyaline cartilage.

The disc derives its structural properties largely through its ability to attract and retain water. The proteoglycans of the nucleus attract water osmotically, exerting a swelling pressure that enables the disc to support spinal compressive loads. The pressurized nucleus also creates tensile pre-stress within the annulus and ligamentous structures surrounding the disc. In other words, although the disc principally supports compressive loads, the fibers of the annulus experience significant tension. As a result, the annular architecture is consistent with current remodeling theories, where the ±60° orientation of the collagen fibers, relative to the longitudinal axis of the spine, is optimally arranged to support the tensile stresses developed within a pressurized cylinder. This tissue pre-stress contributes significantly to the normal kinematics and mechanical response of the spine.

When the physical stress placed on the spine exceeds the nuclear swelling pressure, water is expressed from the disc, principally through the semipermeable cartilaginous end-plates. Consequently, significant disc water loss can occur over the course of a day due to activities of daily living. For example, the average diurnal variation in human stature is about 19 mm, which is mostly attributable to changes in disc height. This change in stature corresponds to a change of about 1.5 mm in the height of each lumbar disc. Using cadaveric spines, researchers have demonstrated that under sustained loading, intervertebral discs lose height, bulge more, and become stiffer in compression and more flexible in bending. Loss of nuclear water also dramatically affects the load distribution internal to the disc. In a healthy disc under compressive loading, compressive stress is created mainly within the nucleus pulposus, with the annulus acting primarily in tension. Studies show that, after three hours of compressive loading, there is a significant change in the pressure distribution, with the highest compressive stress occurring in the posterior annulus. Similar pressure distributions have been noted in degenerated and denucleated discs as well. This reversal in the state of annular stress, from physiologic tension due to circumferential hoop stress, to non-physiologic axial compression, is also noted in other experimental, analytic and anatomic studies, and clearly demonstrates that nuclear dehydration significantly alters stress distributions within the disc as well as its biomechanical response to loading.

The most consistent chemical change observed with degeneration is loss of proteoglycan and concomitant loss of water. This dehydration of the disc leads to loss of disc height. In addition, in humans there is an increase in the ratio of keratan sulphate to chondroitin sulphate, an increase in proteoglycan extractability, and a decrease in proteoglycan aggregation through interaction with hyaluronic acid (although the hyaluronic acid content is typically in excess of that needed for maximum aggregation). Structural studies suggest that the non-aggregable proteoglycans lack a hyaluronate binding site, presumably because of enzytruitic scission of the core protein by stromelysin, an enzyme which is thought to play a major role in extracellular matrix degeneration. These proteoglycan changes are thought to precede the morphological reorganization usually attributed to degeneration. Secondary changes in the annulus include fibrocartilage production with disorganization of the lamellar architecture and increases in type II collagen.

Currently, there are few clinical options to offer to patients suffering from these conditions. These clinical options are all empirically based and include (1) conservative therapy with physical rehabilitation and (2) surgical intervention with possible disc removal and spinal fusion. In contrast to other joints, such as the hip and knee, very few methods of repair with restoration of function are not available for the spine.

Therefore, there is a need for a minimally invasive treatment for degenerated discs which can repair and regenerate the disc. The present invention satisfies that need, as well as others, and overcomes the deficiencies associated with conventional implants and treatment methods.

BRIEF SUMMARY OF THE INVENTION

The present invention comprises an implant and minimally invasive method of treating degenerated discs which can repair and regenerate the disc. More particularly, the present invention comprises a bioactive/biodegradable nucleus implant and method of use. The implant is inflated inside the nucleus space after the degenerated nucleus has been removed to re-pressurize the nuclear space within the intervertebral disc. Nuclear pressure produces tension in the annular ligament that increases biomechanical stability and diminishes hydrostatic tissue pressure that can stimulate fibrochondrocytes to produce inflammatory factors. The device will also increase disc height, separate the vertebral bodies and open the spinal foramina.

By way of example, and not of limitation, an implant according to the invention comprises a collapsible, textured or smooth membrane that forms an inflatable balloon or sack. To inflate the implant, the implant is filled with a high molecular weight fluid, gel or combination of fluid and elastomer, preferably an under-hydrated HA hydrogel/growth factor mixture with or without host cells. Integral to the membrane is a self-sealing valve that allows one-way filling of the implant after it is placed within the disc. The implant membrane is made from a material that allows fibrous in-growth thereby stabilizing the implant. A variety of substances can be incorporated into the device to promote healing, prevent infection, or arrest pain. The implant is inserted utilizing known microinvasive technology. Following partial or total nucleotomy with a small incision, typically annular, the deflated implant is inserted into the nuclear space through a cannula. The implant is then filled through a stem attached to the self-sealing valve. Once the implant is filled to the proper size and pressure, the cannula is removed and the annular defect is sealed.

One of the main difficulties in repairing the degenerated disc is increasing the disc height. The disc and surrounding tissues such as ligaments provide a great deal of resistance to disc heightening. For this reason it is unlikely that placing a hydrogel alone into the nuclear space will be able to generate enough swelling pressure to regain significant disc height. The present invention, however, addresses this problem by allowing initial high pressures to be generated when the implant is inflated in the nuclear space. The initial high pressure is sufficient to initiate the restoration of the original disc height. This initial boost in disc height facilitates the later regeneration stages of this treatment.

In the long term, having a permanent pressurized implant is not likely to be ideal because it may not be able to mimic the essential biomechanical properties of the normal disc. However, the invention also addresses this issue by using a biodegradable sack. The initially impermeable membrane permits high pressurization. When the membrane biodegrades, it allows the hydrogel mixture to take action in playing the role of the normal nucleus pulposus with its inherent swelling pressure and similar mechanical properties.

A variety of growth factors or other bioactive agents can be attached to the surface of the implant or included in the hydrogel mixture that is injected inside the implant. The membrane could be reinforced or not reinforced with a variety of fiber meshes if necessary. Furthermore, a variety of materials could be used for the membrane; the only requirement is that they be biodegradable such that the membrane is impermeable when initially implanted and until it biodegrades. A variety of materials could be injected into the sack such as cartilage cells, alginate gel, and growth factors.

An advantage of the invention is to provide for minimally invasive disk repair.

Another advantage of the invention is to provide a biodegradable implant.

Another advantage of the invention is to provide for restoration of disc height and normal disc biomechanics.

Another advantage of the invention is to provide for disk repair with no loss of mobility.

Another advantage of the invention is to provide for strong integration of an implant with surrounding tissue.

Another advantage of the invention is to provide for disk repair through the use of a very small incision in the annulus.

Another advantage of the invention is to provide an implant that has a bioactive surface.

Another advantage of the invention is to provide for disk repair with very low risk of re-herniation.

Another advantage of the invention is to provide a minimally invasive treatment for degenerated discs which can repair and regenerate the disc.

Another advantage of the invention is to provide a bioactive/biodegradable nucleus implant which can be inflated inside the nucleus space, such as after the degenerated nucleus has been removed.

Further advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 1 is a side view of an implant according to the present invention, shown in a collapsed state.

FIG. 2 is a side view of the implant of FIG. 1, shown in an inflated state, with a portion of the membrane cut away to show the internal filler material.

FIG. 3 is cross-sectional side view of the implant of FIG. 1, shown in the inflated state and showing the integral, internal fill valve.

FIG. 12 is a perspective view of an introducer sheath according to the invention with a trocar inserted and positioned in the nuclear space of an intervertebral disc so as to create an annular opening in the disc.

DETAILED DESCRIPTION OF THE INVENTION

Figure 4:
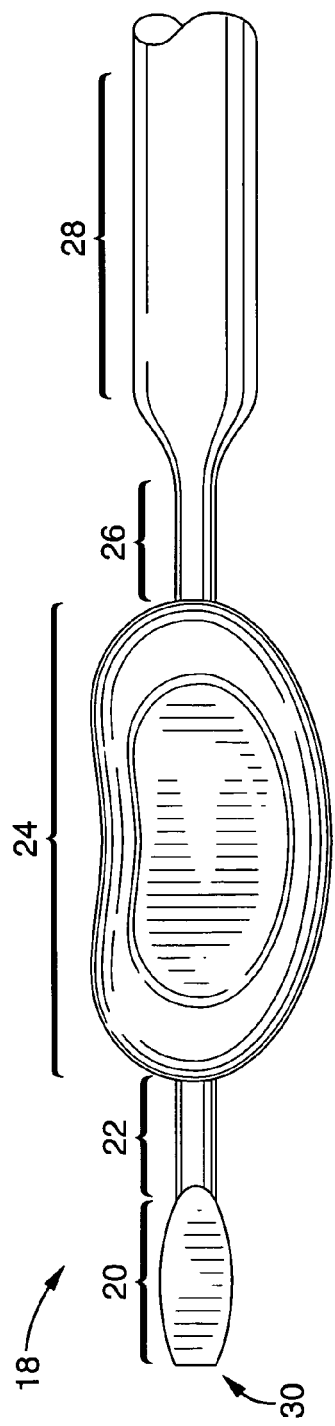
FIG. 4 is a side view of a mandrel for molding an implant according to the present invention.

For illustrative purposes, the present invention is embodied in the method and apparatus described herein and generally shown in FIG. 1 through FIG. 24. It will be appreciated that the apparatus may vary as to configuration and as to details of the structure, and that the method may vary as to the specific steps and sequence, without departing from the basic concepts as disclosed herein.

Referring first to FIG. 1 through FIG. 3, an implant 10 according to the present invention comprises a collapsible membrane 12 that is formed into a inflatable balloon or sack that will conform to the shape of the nucleus pulposus when inflated. Membrane 12 preferably comprises an inert material such as silicone or a similar elastomer, or a biodegradable and biocompatible material such as poly (DL-lactic-co-glycolic acid; PLGA). Since the implant will serve as an artificial inner annulus, and its internal chamber will contain a pressurized nuclear filler material 14 used for inflation, the membrane material should be relatively impermeable while possessing the necessary compliance and strength. In addition, the membrane material should be sufficiently flexible so that the implant can easily be passed through a surgical catheter or cannula for insertion.

Table 1 compares certain characteristics of the inner annulus to a number of commercially-available elastomers that were considered for the membrane material. Key design requirements were biocompatibility, stiffness, and elongation-to-failure. While any of these materials, as well as other materials, can be used, our preferred material was aliphatic polycarbonate polyurethane (HT-4) which has a stiffness that closely approximates that of the inner annulus, can be fabricated into complex shapes using dip molding, possess significant failure properties, and has a track-record for in vivo use.

The peripheral surface of the implant is preferably coated with one or more bioactive substances that will promote healing of the inner annulus and integration of the implant with the surrounding annular tissue. Also, the top and bottom surfaces of the implant are preferably coated with one or more bioactive substances that will promote healing of the cartilaginous endplates and integration of the implant with the endplates.

To limit the amount of lateral bulging when the implant is axially compressed, the peripheral surface of the implant can be reinforced with a fiber matrix if desired. In that event, the angle of the fibers relative to the vertical axis of placement should be approximately ±60° to closely approximate that of the native collagen fibers in the inner annulus.

Implant 10 includes an integral, internal, self-sealing, one-way valve 16 that will allow the implant to be inserted in a deflated state and then be inflated in situ without risk of deflation. Valve 16 functions as a flapper valve to prevent leakage and maintain pressurization of the implant when pressurized with the nuclear filler material. Because valve 16 is internal to the implant, compression of implant 10 will place internal pressure on valve 16 to keep it in a closed position. Due to the self-sealing nature of valve 16, the same pressure that might be sufficient to allow the nuclear filler material to escape will cause valve 16 to remain closed so as to create a barrier to extrusion.

To better understand the operation and configuration of valve 16, reference is now made to FIG. 4 which shows the preferred embodiment of a mandrel 18 for fabricating the implant. Mandrel 18 preferably comprises a planar stem portion 20, a first cylindrical base portion 22, a mold portion 24, a second cylindrical base portion 26, and a shank 28. To fabricate an implant, distal end 30 of the mandrel is dipped in a bath of membrane material to a defined depth which is generally at a point along second base portion 26 and molded to a thickness between approximately 5 mils and 7 mils.

Figure 5:
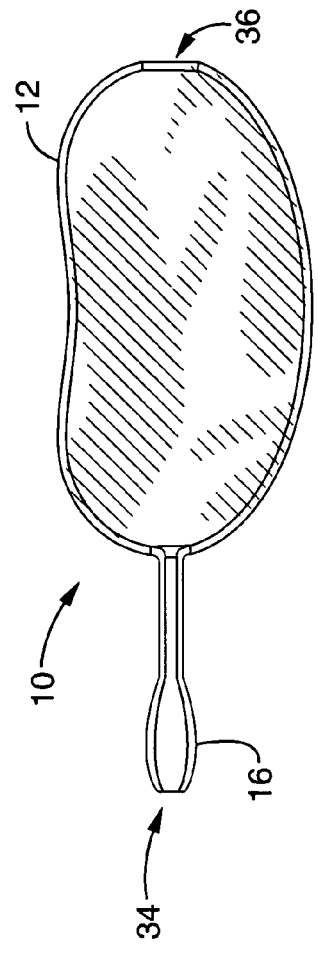
FIG. 5 is a side view of an implant membrane according to the present invention as it would be seen after being dip molded on the mandrel shown in FIG. 4 but before removal from the mandrel.
Figure 7:
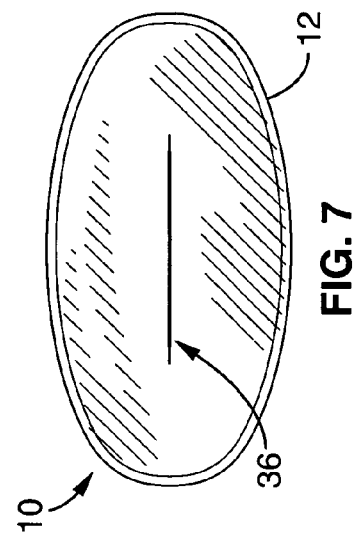
FIG. 7 is an end view of the implant shown in FIG. 5 after heat-sealing the open end.
Figure 6:
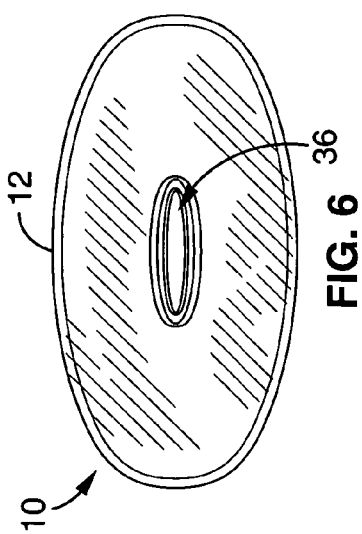
FIG. 6 is an end view of the implant shown in FIG. 5 prior to heat-sealing the open end.

FIG. 5 generally depicts the configuration of the implant after it has dried on the mandrel. However, the mandrel is not shown in FIG. 5 so that the implant can be more clearly seen. After the membrane material dries on the mandrel, it is drawn off of the mandrel by rolling it toward distal end 30 As a result, the membrane is turned inside-out. By inverting the membrane in this manner, the portion of membrane material that coated stem portion 20 becomes valve 16 which is now located inside the implant as shown in FIG. 3. The portion of membrane material that coated first base portion 22 becomes an entrance port 32 into valve 16. Note that the distal end 34 of valve 16 was sealed during molding, while the distal end 36 of the implant is still open as shown in FIG. 5 and FIG. 6. Accordingly, to finish the fabrication process, distal end 36 of the implant is heat-sealed to close it off as shown in FIG. 7.

To inflate the implant, a needle-like fill stem is inserted through entrance port 32 so as to puncture the distal end 34 of valve 16 and extend into the interior chamber of the implant. The implant is then filled with a fluid material, such as a high molecular weight fluid, gel or combination of fluid and elastomer which has a viscosity that will permit its introduction into the implant through, for example, an 18-gauge needle. The specific properties of filler material 14 should allow the material to achieve and maintain the desired osmotic pressure. The filling takes place after the implant is placed within the disc. Preferably filler material is a cross-linkable polyethylene glycol (PEG) hydrogel with chondroitin sulfate (CS) and hyaluronic acid (HA) with or without host cells as will now be described.

Table 2 shows the characteristics of a number of commercially-available hydrogels that were considered for filler material 14. While any of these materials, as well as other materials, can be used, we selected an in situ cross-linkable polyethylene glycol (PEG) gel because of its bio-compatibility and physical properties. The PEG gel is a two component formulation that becomes a low-viscosity fluid when first mixed and which cross-links to a firm gel after insertion. The cross-link time depends on the formulation. A key feature of the gel is its osmotic pressure. We sought to formulate a gel that would possess an osmotic pressure of near 0.2 MPa which is that of the native nucleus pulposus.

The preferred PEG gel comprises a nucleophilic "8-arm" octomer (PEG-$NH_2$, MW 20 kDa) and a "2-arm" amine-specific electrophilic dimer (SPA-PEG-SPA, MW 3.4 kDa), and is available from Shearwater Corporation, Huntsville, Ala. The addition-elimination polymerization reaction culminates in a nitrogen-carbon peptide-like linkage, resulting in a stable polymer whose rate of polymerization increases with pH and gel concentration. The range of pH (approximately 10 for the unmodified gel) and concentration (approximately 0.036 g/mL to 0.100 g/mL) investigated resulted in a polymerization time of approximately 10 minutes to 20 minutes. To fortify the hydrogel's inherent swelling due to hydrogen bonding, high molecular weight additives chondroitin sulfate (CS) and hyaluronic acid (HA) with established fixed charged densities were incorporated into the gel matrix.

The swelling pressures of the hydrogel filler (cross-linked polyethylene glycol (PEG) hydrogels and derivatives incorporating HA and CS) were measured by equilibrium dialysis as a function of gel and additive concentration. Polyethylene glycol (Molecular Weight 20 kDa available from Sigma-Aldrich Corporation) was also used as the osmotic stressing agent, while molecularporous membrane tubing was used to separate sample gels from the dialysate. Gels were formed over a broad concentration range (0.036 to 0.100 g/mL), weighed, placed in dialysis tubing (Spectra/Por Membrane, Molecular Weight Cut Off of 3.5 kDa available from Spectrum Medical Industries), and allowed to equilibrate for 40 to 50 hours in the osmotic stressing solution, weighed again to determine hydration, then oven dried (at 60 degrees Celsius) and weighed once again. Hydration values taken at various osmotic pressures allowed the construction of osmotic pressure curves. By adjusting the concentrations of CS or HA we were able to meet our design criteria, successfully achieving swelling pressures above 0.2 MPa. A potential deleterious interaction between the elastomer and hydrogel was noted. One PEG-CS specimen aged in saline demonstrated breakdown of the elastomer shell. This may have been due to the relatively low-molecular weight CS penetrating into the membrane material (polyurethane) leading to an increased rate of hydrolysis.

Figure 8:
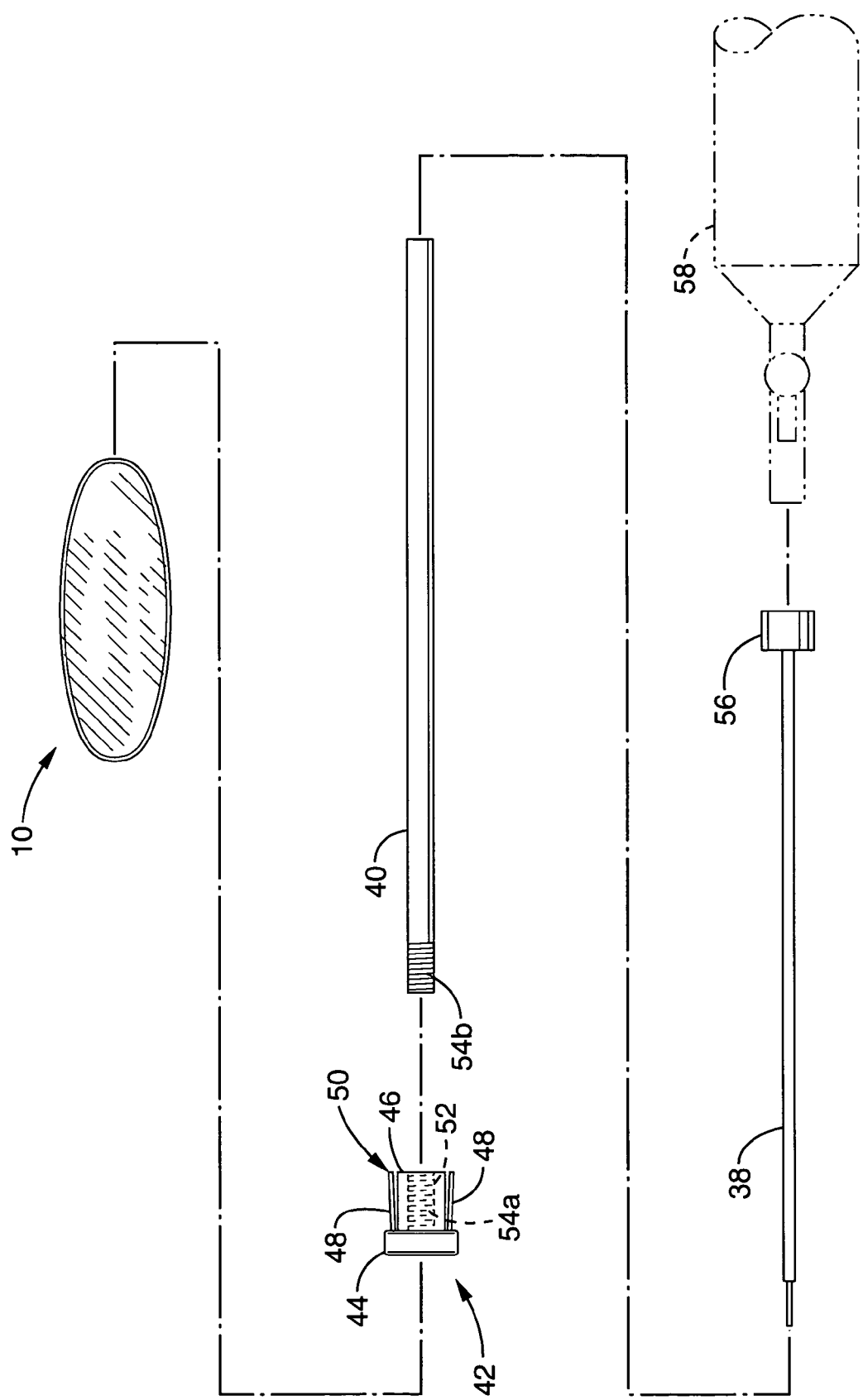
FIG. 8 is an exploded view of a delivery system for placement of an implant according to the invention shown in relation to the implant.
Figure 9:
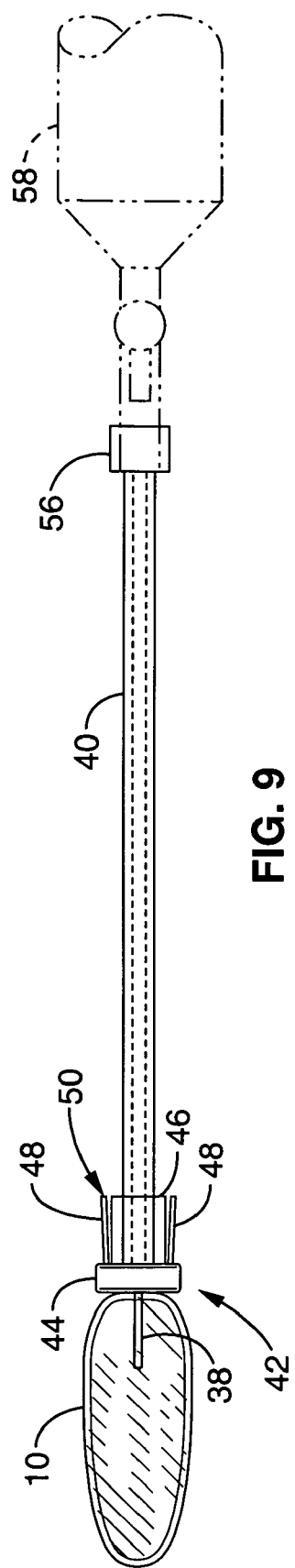
FIG. 9 is an assembled view of the delivery stem shown in FIG. 8 with the implant attached.

Referring now to FIG. 8 and FIG. 9, the invention includes an implant delivery system comprising a hollow implant fill stem 38, a hollow buttress positioner 40, and an inner annular buttress 42. Implant fill stem 38 is configured for inflating implant 10 after insertion, and inner annular buttress 42 is configured to extend into and block a hole 66 (see FIG. 11A) that is made in the annulus for insertion of implant 10. Once inserted, inner annular buttress 42 prevents extrusion of the implant during spinal loading. Inner annular buttress 42 preferably comprises a polymer head portion 44 of suitable diameter for plugging hole 66, a smaller diameter polymer body portion 46 extending from head portion 44, and metal barbs or pins 48 having ends 50 that extend outward in relation to body portion 46 such that they will engage the annulus to prevent expulsion of inner annular buttress 42 (and implant 10 during spinal loading. Pins 48, which can be formed of stainless steel, Nitinol®, or the like, can be molded or otherwise inserted into head portion 44 for retention therein.

An inner passage 52 extends through inner annular buttress 42 for attachment to buttress positioner 40 and insertion of fill stem 38 through inner annular buttress 42 into implant 10. Inner passage 52, head portion 44 and body portion 46 are preferably coaxial. Buttress positioner 40 and inner annular buttress 42 are coupled together using mating threads 54a, 54b or another form of detachable coupling that allows buttress positioner 40 to be easily removed from inner annular buttress 42 after placement. Note that inner annular buttress 42 can be attached to implant 10 using adhesives, ultrasonic welding or the like, or can be separate and unattached from implant 10.

Fill stem 38 includes a collar 56 for attachment to a syringe 58 or other device to be used for inflating the implant with the filler material. Fill stem 38 and syringe 58 are coupled together using threads (not shown) or another form of detachable coupling. Preferably, syringe 58 includes a pressure gauge (not shown) for determining the proper inflation pressure. The implant and delivery system would be deployed into the nucleus pulposus space by being inserted into a conventional catheter, cannula or the like (not shown) having a retractable cover (not shown) that protects the implant during insertion.

Figure 10:
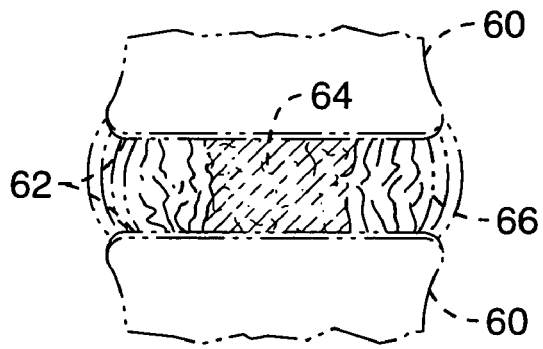
FIG. 10 is a side schematic view of a degenerated intervertebral disc prior to repair using an implant according to the present invention.

FIG. 10 depicts the vertebral bodies 60, cartilage endplates 62, degenerated nucleus 64, and degenerated annulus 66 in the spine. The indications for use of the implant are a patient with back pain or radiating pain down the leg where the cause of the pain has been determined to be a herniated disc which is impinging on the surrounding spinal nerves. Deployment of the implant is preferably according to the following surgical procedure shown in FIG. 11A through FIG. 11G which is minimally invasive.

Figure 11A:
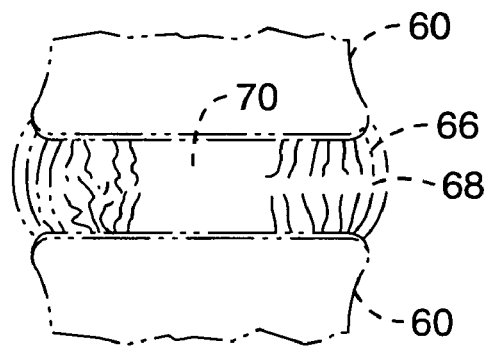
FIG. 11A through FIG. 11G is a flow diagram showing a surgical procedure for placement of an implant according to the present invention.

As shown in FIG. 11A, the first step in the surgical procedure is to perform a minimally invasive postero-lateral percutaneous discectomy. This is executed by making a small hole 68 through the annulus fibrosus of the intervertebral disc and removing the nucleus pulposus tissue through that hole. Several technologies were considered to facilitate removing degenerated nuclear material through a small opening made through the annulus fibrosus. The most promising technology is the ArthroCare Coblation probe (ArthroCare Spine, Sunnyvale, Calif.). This device vaporizes the nucleus in situ. Because of density differences that exist between the nucleus and annulus, the Coblation probe removes the less-dense nuclear material more easily than the annulus. This allows the surgeon to remove the nuclear material while minimizing damage to the remaining annulus or adjacent vertebral body.

The referred protocol for creating a nuclear space for the implant comprises making a small puncture within the annulus with a pointed, 3 mm diameter probe. This pointed probe serves to separate annular fibers and minimize damage to the annulus. Next, a portion of the nucleus is removed using standard surgical instruments. The Coblation probe is then inserted. Suction and saline delivery are available with the probe, although we have found that suction through another portal using, for example, a 16-gage needle, may be required. A critical feature of device success is the method of creating a nuclear space while minimizing trauma to the outer annulus fibrosus. The outer annulus should be preserved, as it is responsible for supporting the implant when pressurized.

Figure 11B:
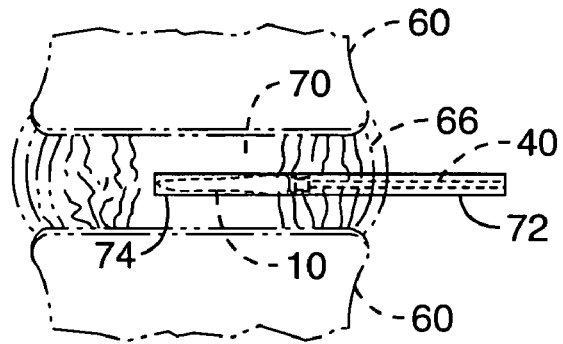
Figure 11C:
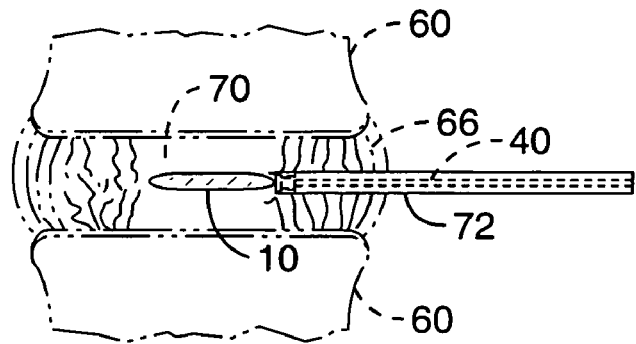
Figure 11D:
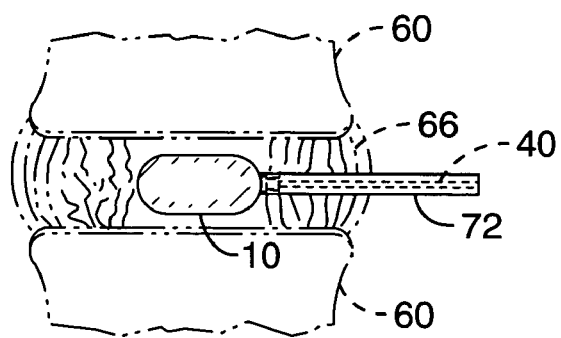
Figure 11E:
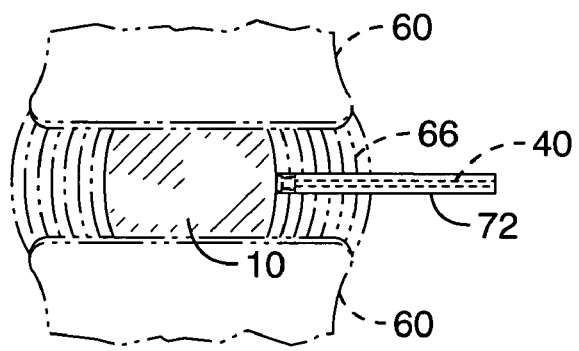

Next, as shown in FIG. 11B, the deflated implant 10 is inserted into the empty nuclear space 70. This is accomplished by inserting the implant through a conventional insertion catheter (cannula) 72. Note that fill stem 38, buttress positioner 40 and inner annular buttress 42 are also inserted through catheter 72, which also results in compression of pins 48. The cover 74 on the insertion catheter 72 is then retracted to expose the implant as shown in FIG. 11C. Next, as shown in FIG. 11D, the implant is inflated with the filler material 14, until it completely fills the nuclear space 70. FIG. 11E shows the implant fully inflated. Note the resultant increase in disc height and restoration of tensile stresses in the annulus. The pressurized implant initiates the restoration of the original biomechanics of the healthy disc by increasing the disc height, relieving the annulus of the compressive load, and restoring the normal tensile stress environment to the annulus. The restoration of the normal tensile stress environment in the annulus will promote the annular cells to regenerate the normal annulus matrix.

Figure 11F:
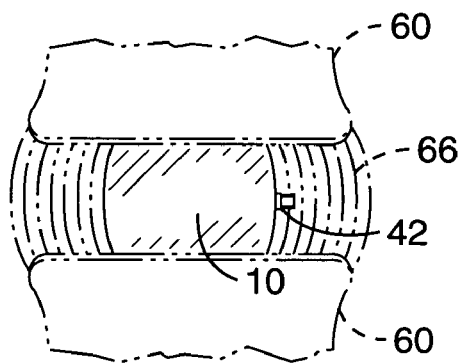

The catheter and delivery system (e.g., fill stem 38 and buttress positioner 40) are then removed, leaving inner annular buttress 42 in place and implant 10 sealed in position as shown in FIG. 11F. Note that inner annular buttress 42 not only serves to align and place the implant, but prevents extrusion during spinal loading. In addition, the one-way valve 16 in the implant prevents the hydrogel/growth factor mixture from leaking back out of the nucleus implant. Therapeutic agents on the peripheral and top/bottom surfaces of the implant stimulate healing of the inner annulus and cartilage endplates. In addition the surface growth factors will also promote integration of the implant with the surrounding tissue.

Figure 11G:
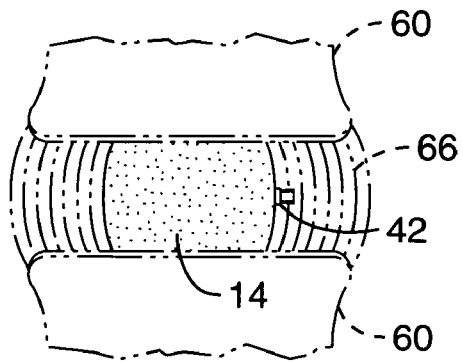

Finally, FIG. 11G depicts the implant biodegrading after a predetermined time so as to allow the hydrogel/growth factor mixture to play its bioactive role. The hydrogel is hydrophilic and thereby attracts water into the disc. Much like the healthy nucleus pulposus, the hydrogel creates a swelling pressure which is essential in normal disc biomechanics. The growth factor which is included in the hydrogel stimulates cell migration, and proliferation. We expect the environment provided for these cells to stimulate the synthesis of healthy nucleus pulposus extracellular matrix components (ECM). These cells will thereby complete the regeneration of the nucleus pulposus.

It will be appreciated that the implant can be inserted using other procedures as well. For example, instead of performing a discectomy (posterolateral or otherwise), the implant could be inserted into a preexisting void within the annulus that arises from atrophy or other form of non-device-induced evacuation of the nucleus pulposus, such as for, example, by leakage or dehydration over time.

EXAMPLE 1

Prototype implant shells were fabricated by Apex Biomedical (San Diego, Calif.). The fabrication process included dip molding using a custom-fabricated mandrel. The mandrel was dipped so that the elastomer thickness was between 5 and 7 mils (0.13-0.17 mm). After dipping, the implant was removed from the mandrel, inverted (so that the stem was inside the implant) and heat-sealed at the open end. This process resulted in a prototype that could be filled with the PEG gel, which when cross-linked could not exit through the implant stem. The stem effectively sealed the implant by functioning as a "flapper valve". This means that by being placed within the implant, internal pressures (that might serve to extrude the gel) compress and seal the stem, creating a barrier to extrusion. This sealing mechanism was verified by in vitro testing.

EXAMPLE 2

Elastomer bags filled with PEG were compressed to failure between two parallel platens. The implants failed at the heat seal at approximately 250 Newtons force. These experiments demonstrated that under hyper-pressurization, the failure mechanism was rupture at the sealed edge, rather than extrusion of gel through the insertion stem. When the device is placed within the intervertebral disc, support by the annulus and vertebral body results in a significantly increased failure load and altered construct failure mechanism.

EXAMPLE 3

Ex vivo mechanical testing were performed with human cadaveric spines to characterize the performance of the device under expected extreme in vivo conditions. We conducted a series of experiments that consisted of placing the device in human cadaveric discs using the developed surgical protocols and then testing the construct to failure under compressive loading. The objective of these experiments was to characterize the failure load and failure mechanism. The target failure load was to exceed five times body weight (anticipated extremes of in vivo loading). Importantly, the failure mode was to be endplate fracture and extrusion of the implant into the adjacent vertebra. This is the mode of disc injury in healthy spines. We did not want the construct to fail by extrusion through the annulus, particularly through the insertion hole, since this would place the hydrogel in close proximity to sensitive neural structures.

Load-to-failure experiments demonstrated that the implant may sustain in excess of 5000 N (approximately seven times body weight) before failure, and that the failure mode was endplate fracture. These preliminary experiments demonstrate that the implant can sustain extremes in spinal compression acutely.

Referring now to FIG. 12, the nuclear space can be prepared for receiving the implant by removing degenerated nuclear material using a coblation probe or the like as described above. Upon exposing the targeted disc 100, the nuclear space 102 can be accessed via a trocar 104, such as a stainless steel, 7 Fr. OD, trocar with a small Ultem handle 106. Preferably, a corresponding 7 Fr introducer sheath 108 also having a small Ultem handle 110, is used for insertion of the trocar. An example of a suitable introducer sheath is a 7 Fr plastic sheath with 0.003 inch walls and a 1.5 inch working length, such as a modified Cook or equivalent. The trocar is then removed upon access leaving a patient access point. Use of an introducer tends to minimize wear and tear on the hole, thus maximizing engagement of inner annular buttress 42. In the embodiment shown, inner annular buttress 42 would typically have a 0.071 OD and a length of 0.070 inches, and carry three pins 48 having a diameter of approximately 0.008 inches and a length of approximately 0.065 inches.

Figure 13:
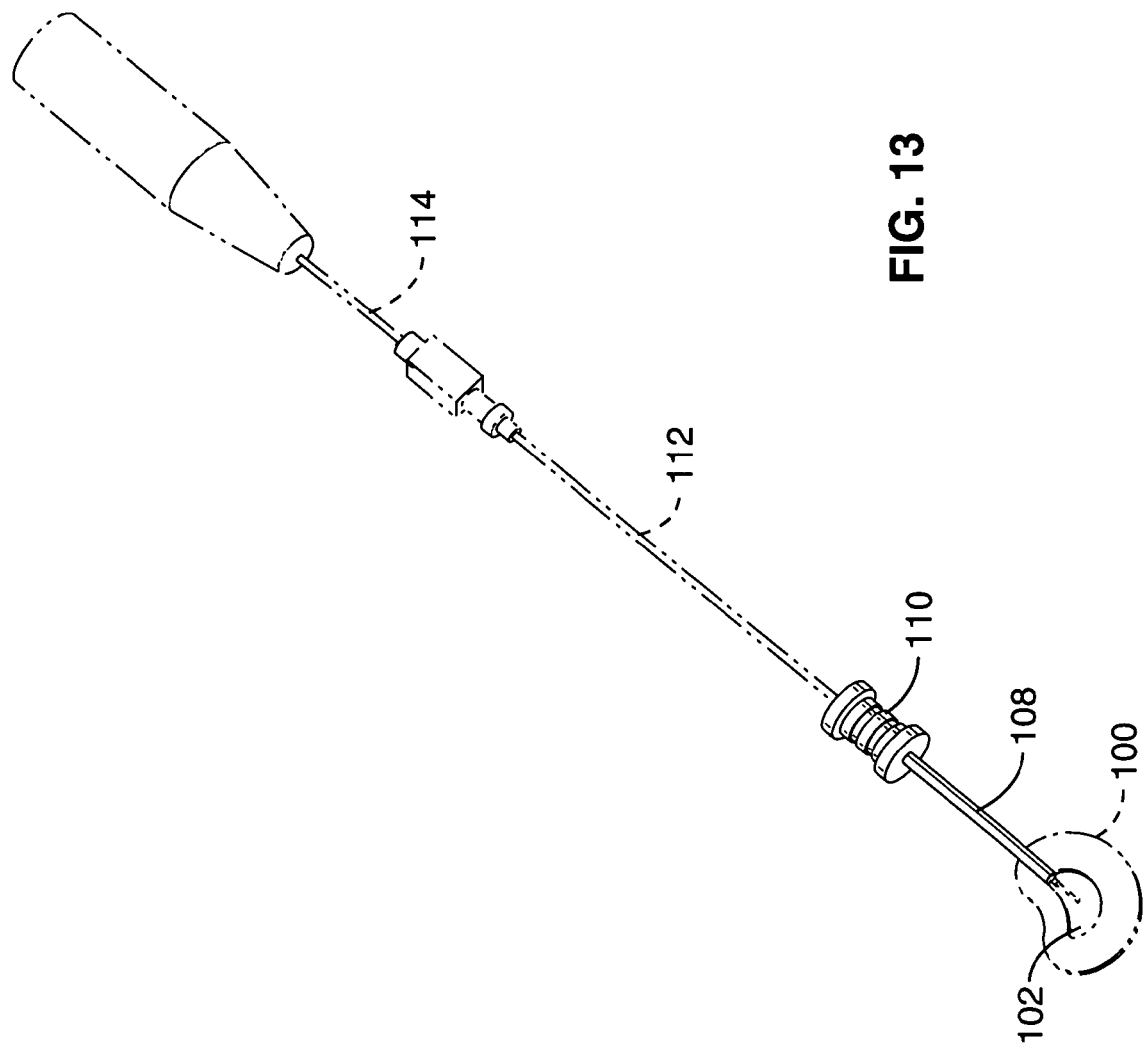
FIG. 13 is a perspective view of a Crawford needle and Spine Wand inserted in the introducer sheath shown in FIG. 12 and positioned for ablation of the nuclear pulposus in an intervertebral disc.
Figure 14:
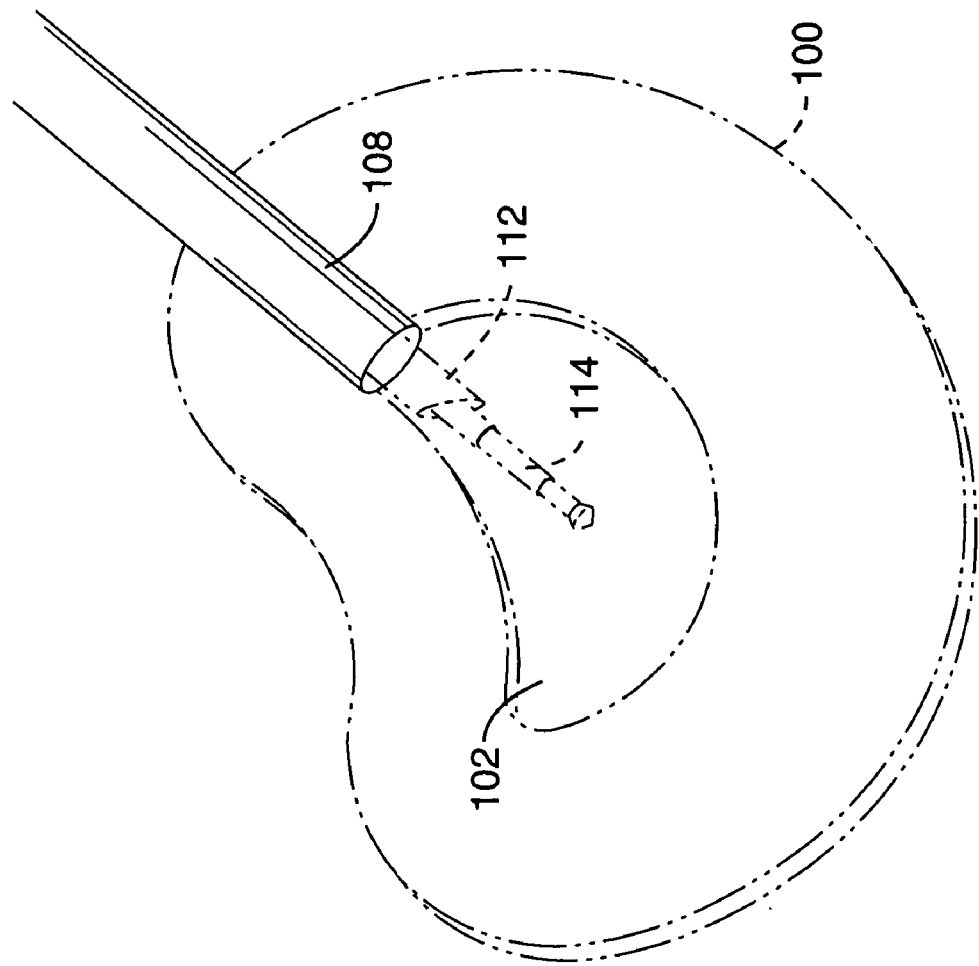
FIG. 14 is a detail view of the implant end portion of the assembly of FIG. 13.

Referring to FIG. 13 and FIG. 14, a Crawford needle 112 (e.g., 17 gage×6 inch, included with the ArthroCare Convenience Pack Catalog No. K7913-010) and ArthroCare PercDLE Spine Wand 114 (ArthroCare catalog number K7813-01) are introduced into the nucleus through the introducer sheath 108 and the nucleus pulposus is ablated. By moving the Wand in and out of the needle, the degree of articulation of the distal tip can be controlled. The Crawford needle also provides added rigidity for improved manipulation of the device.

Figure 15:
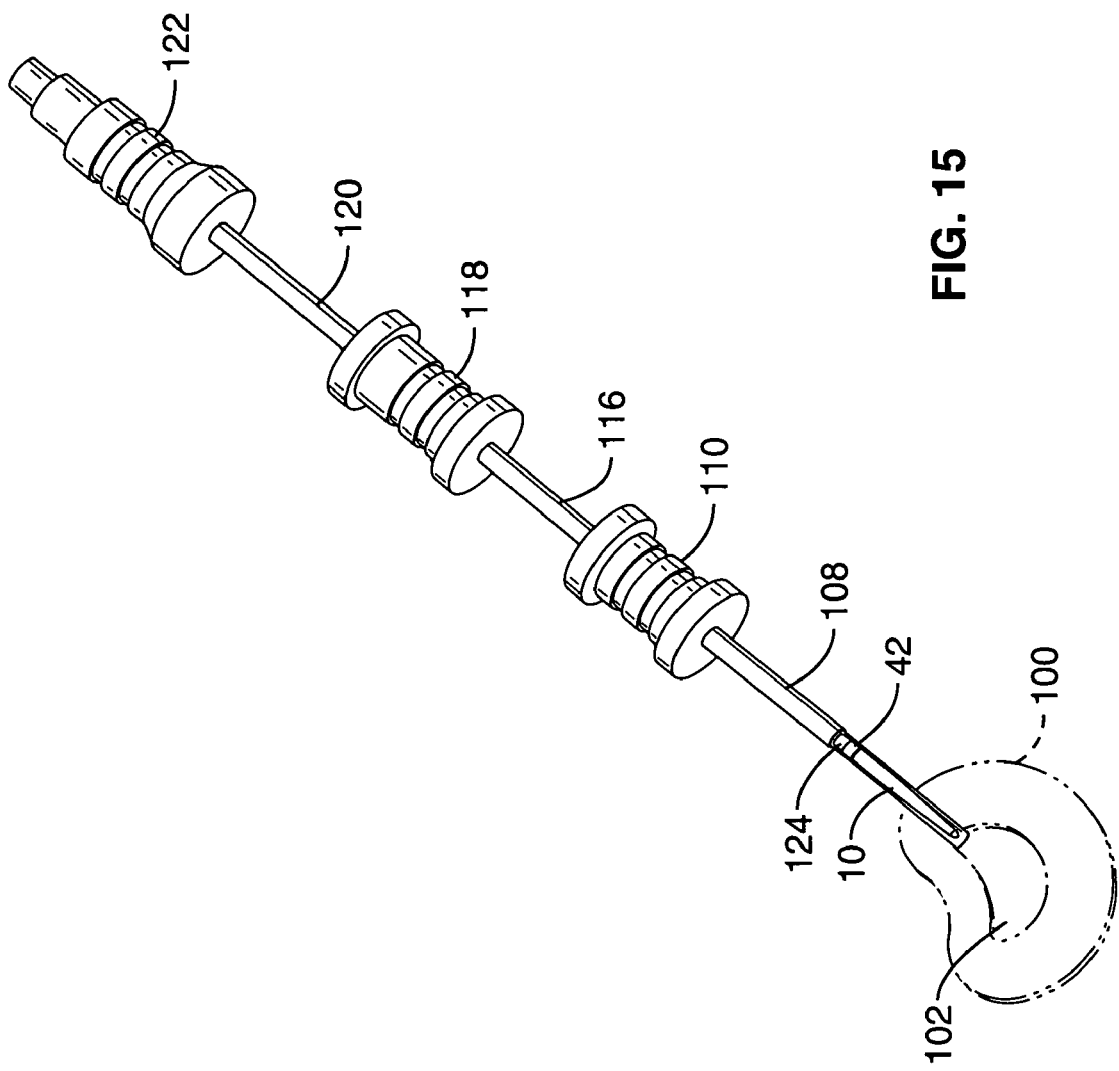
FIG. 15 is a perspective view of an implant launcher and fill assembly according to the present invention shown with an introducer sheath, launcher sheath, fill tube positioned prior to deployment of an implant in the nuclear space of an intervertebral disc and with the proximal end portions of the introducer sheath and launcher sheath partially cut away to expose the implant and buttress.
Figure 16:
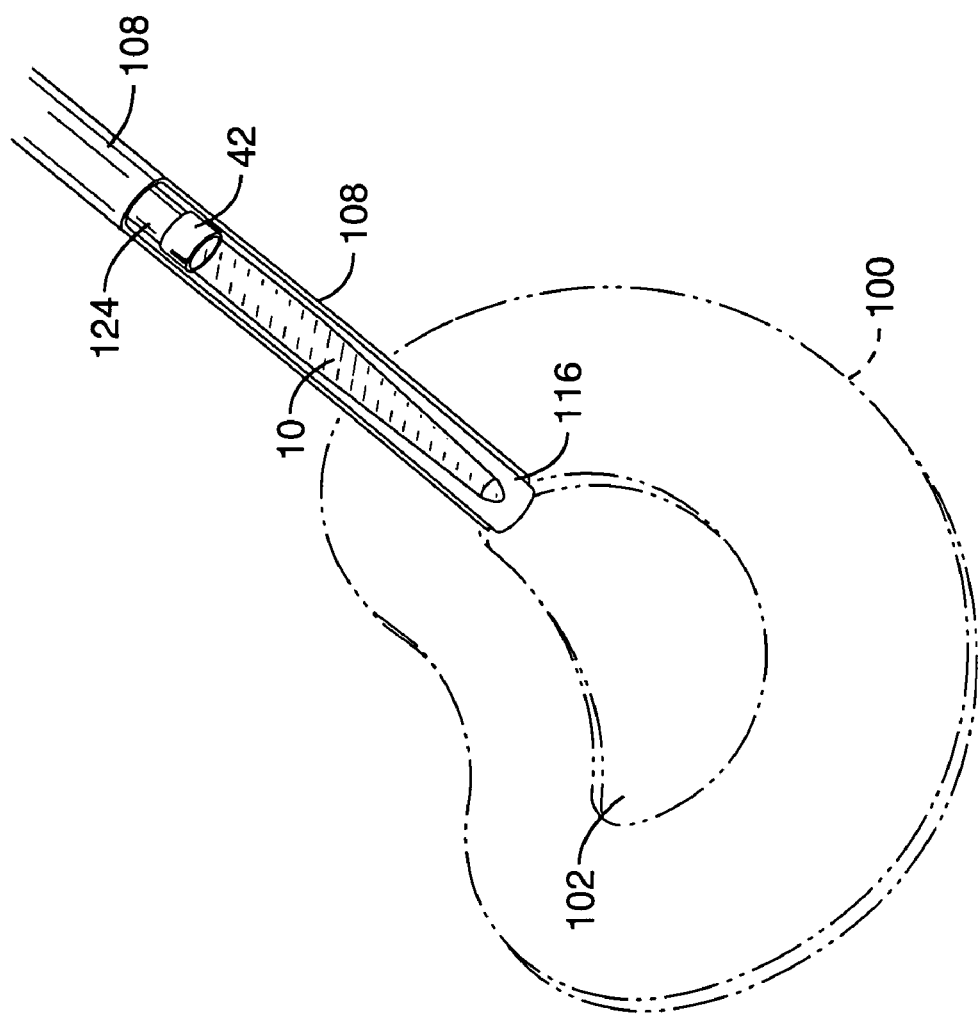
FIG. 16 is a detail view of the implant end portion of the assembly of FIG. 15.

Referring now to FIG. 15 and FIG. 16, an alternative embodiment of the delivery system shown in FIG. 8 and FIG. 9 is illustrated. In this embodiment, introducer sheath 108 is used as a port into the nuclear space 102. In FIG. 15, the end portion of introducer sheath 18 has been cutaway for clarity. A plastic launcher sheath 116 (e.g., 0.084 inch×0.090 inch×3 inch) is slidably insertable into the introducer sheath is provided. Note that the end portion of launch sheath 116 has also been cutaway for clarity. Preferably, launcher sheath 116 includes a small plastic handle 118, and all or a portion of the launcher sheath is preferably flexible to assist with deployment of the implant as described below. A fill tube 120 (e.g., 14 XT×3.9 inch long) is provided that is slidably insertable into launcher sheath 116. Fill tube 120 also preferably includes a small plastic handle 122. The fill tube preferably terminates at its proximal end with a female leur lock 124 having a 0-80 UNF thread to which the assembly of buttress 42 (carrying implant 10) is threadably attached. It will be appreciated that buttress 42 can be attached to leur lock 124 after fill tube 120 has been inserted into launcher sheath 116 and extended therethrough such that leur lock 124 extends through the end of launcher sheath 116. At this point pins 48 can be manually depressed and the un-deployed implant/buttress assembly pulled into the launcher sheath. Alternatively, buttress 42 can be attached to leur lock 124 and fill tube 120 then inserted into launcher sheath 116. With either approach, the assembly of implant 10, buttress 42, launcher sheath 116 and fill tube 120 can then be inserted into introducer sheath 108 and pushed into the nuclear space 102. A small c-clip style spacer or the like (not shown) can be used to maintain separation between handles 118 and 122 to prevent premature deployment of the implant as will be more fully appreciated from the discussion below.

Figure 17:
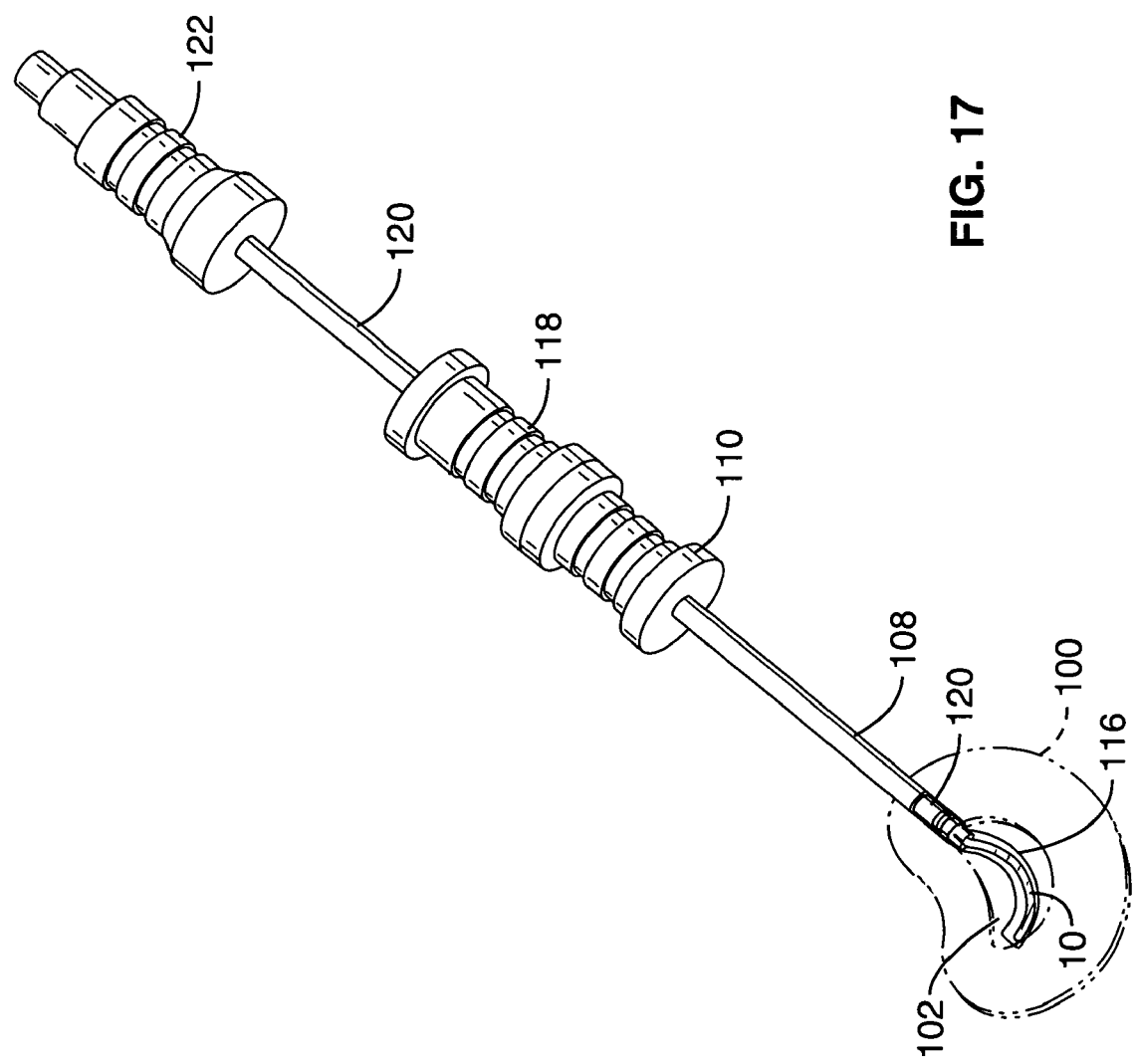
FIG. 17 is a perspective view of the assembly of FIG. 15 after insertion of the implant in the nuclear space of the intervertebral disc.
Figure 18:
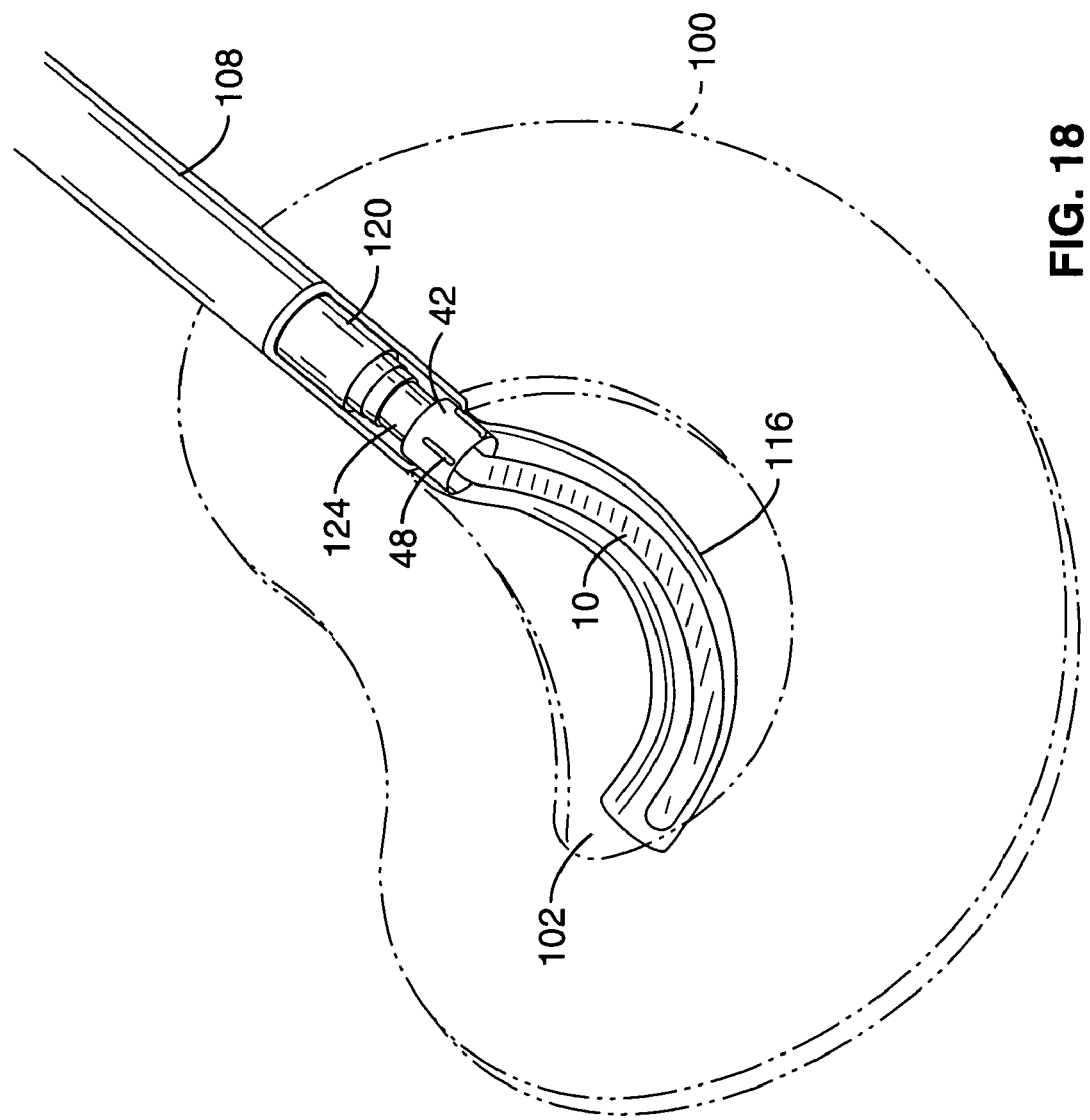
FIG. 18 is a detail view of the implant end portion of the assembly of FIG. 17.
Figure 19:
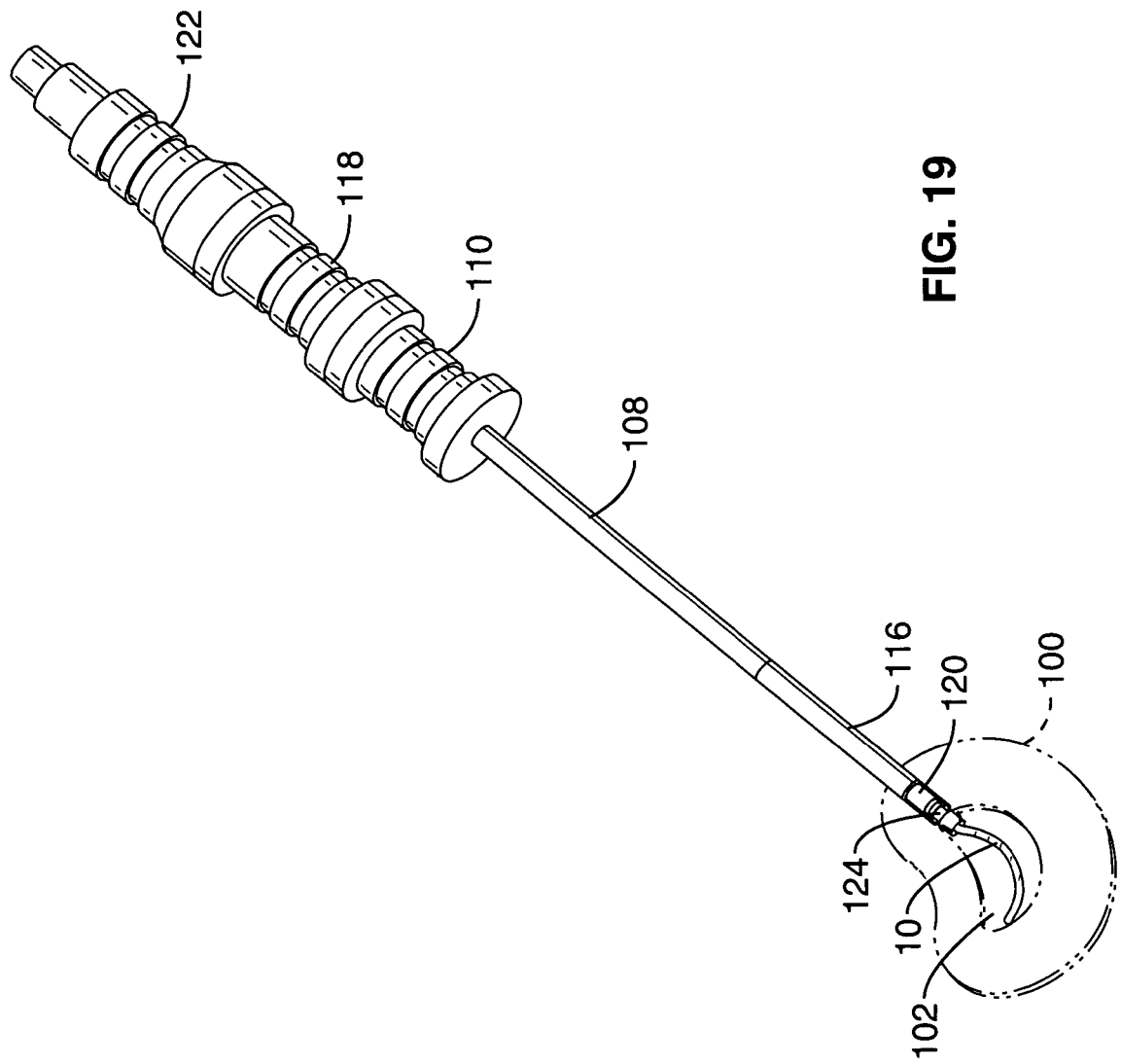
FIG. 19 a perspective view of the assembly of FIG. 15 after deployment of the implant in the nuclear space and prior to retraction of the implant and inner annular buttress.
Figure 20:
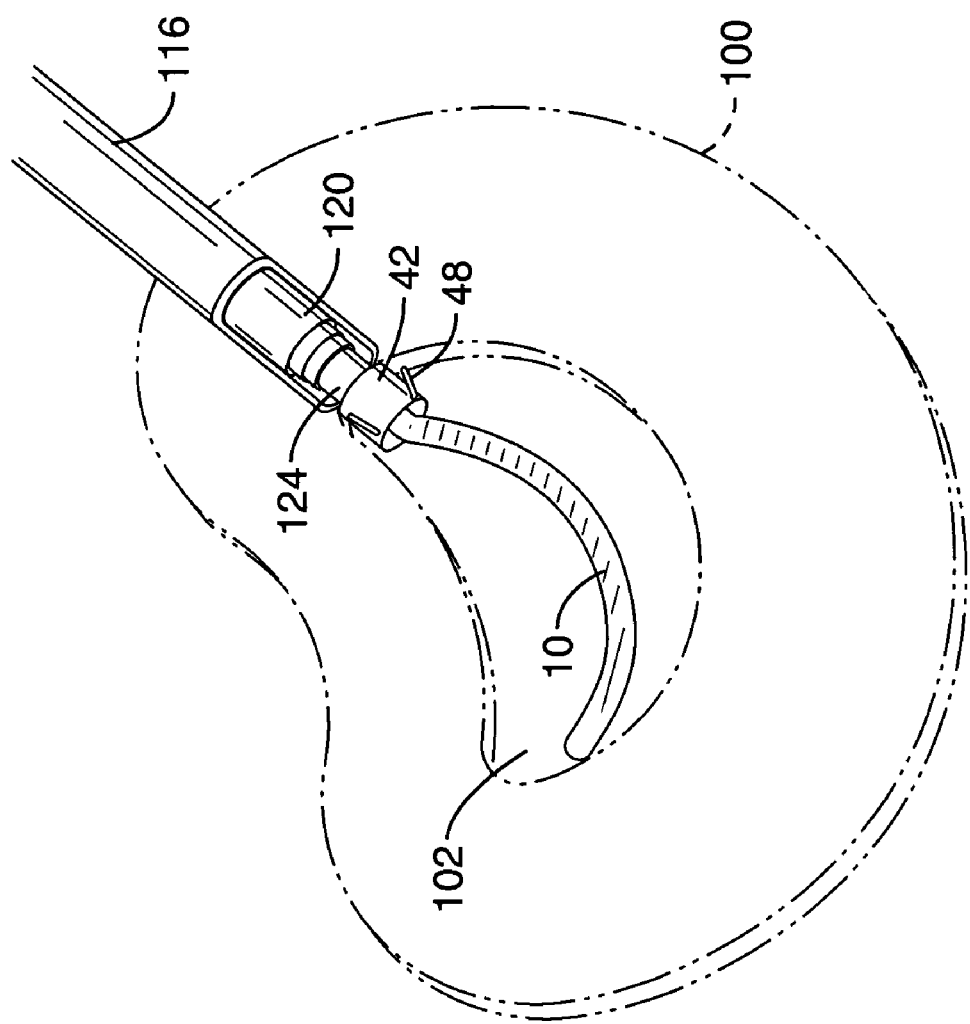
FIG. 20 is a detail view of the implant end portion of the assembly of FIG. 19.
Figure 21:
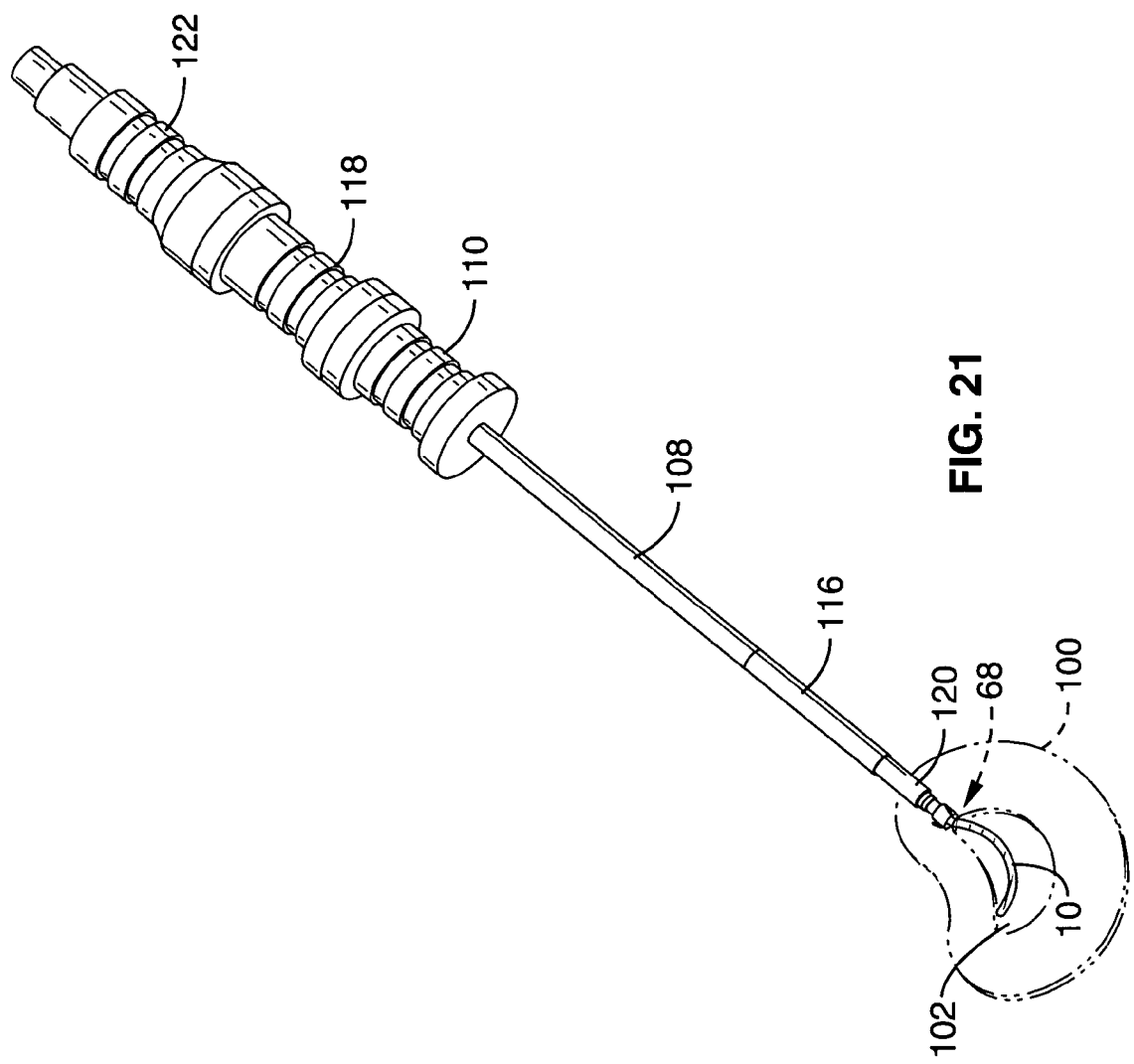
FIG. 21 is a perspective view of the assembly of FIG. 15 after partial retraction of the implant and inner annular buttress with the inner annular buttress shown engaging and plugging the annular opening in the intervertebral disc.
Figure 22:
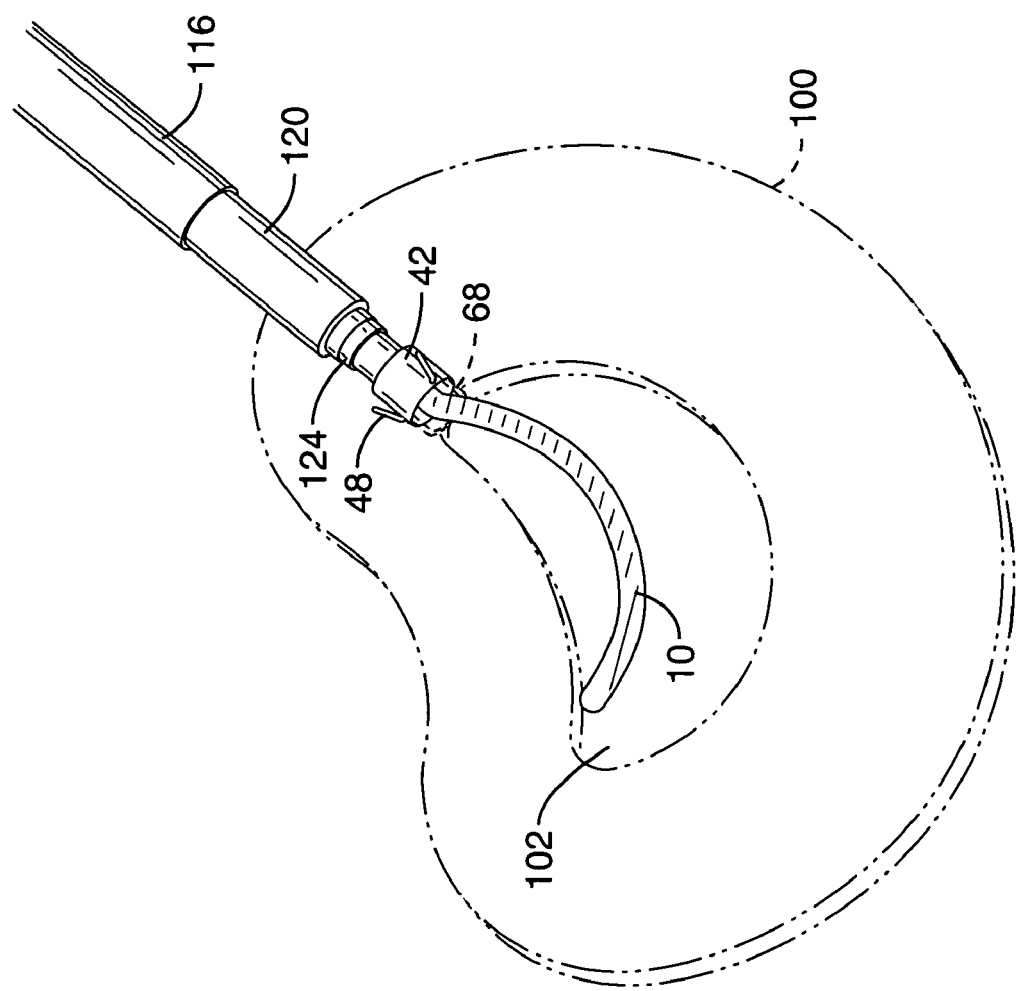
FIG. 22 is a detail view of the implant end portion of the assembly of FIG. 21.
Figure 23:
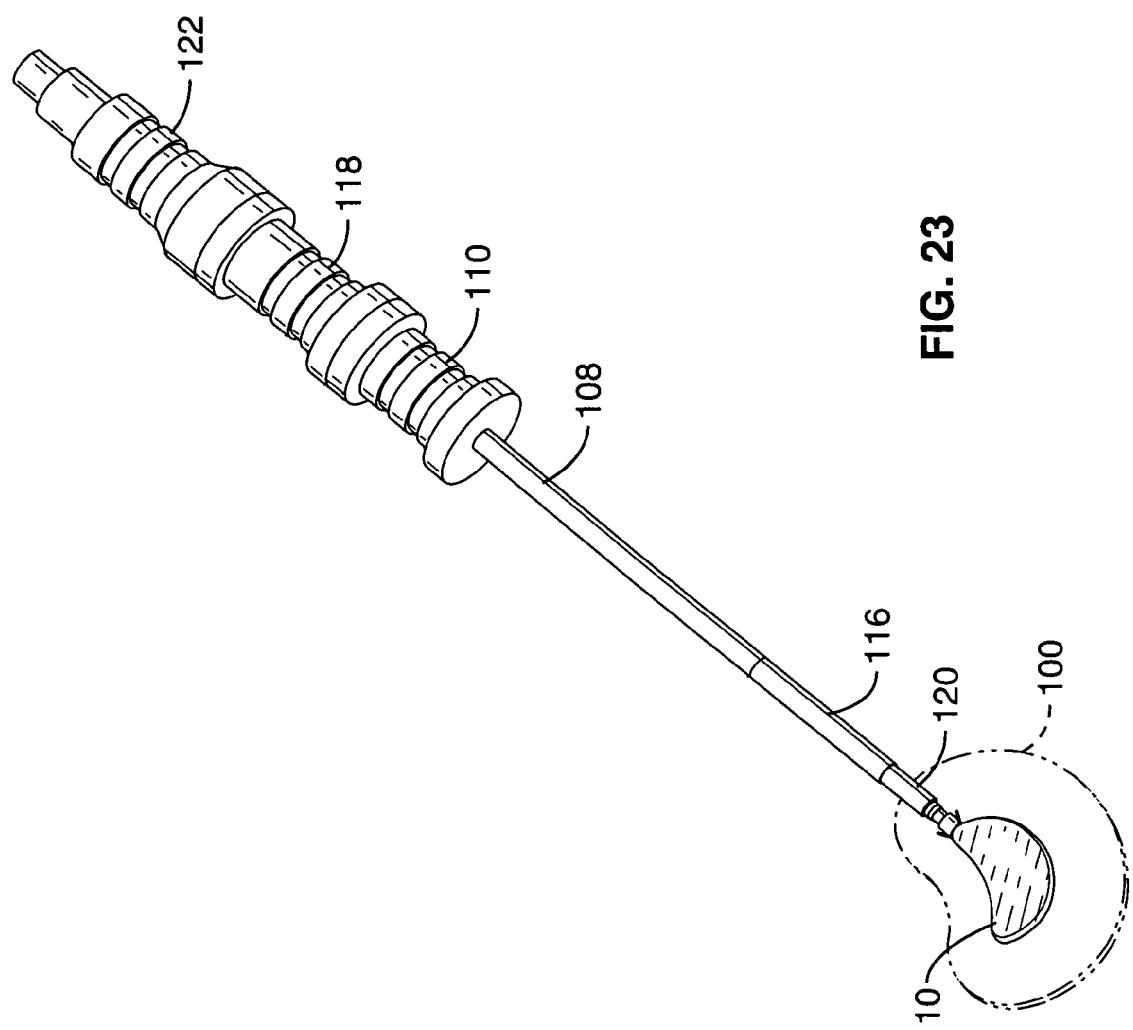
FIG. 23 is a perspective view of the assembly of FIG. 15 after the implant is inflated.
Figure 24:
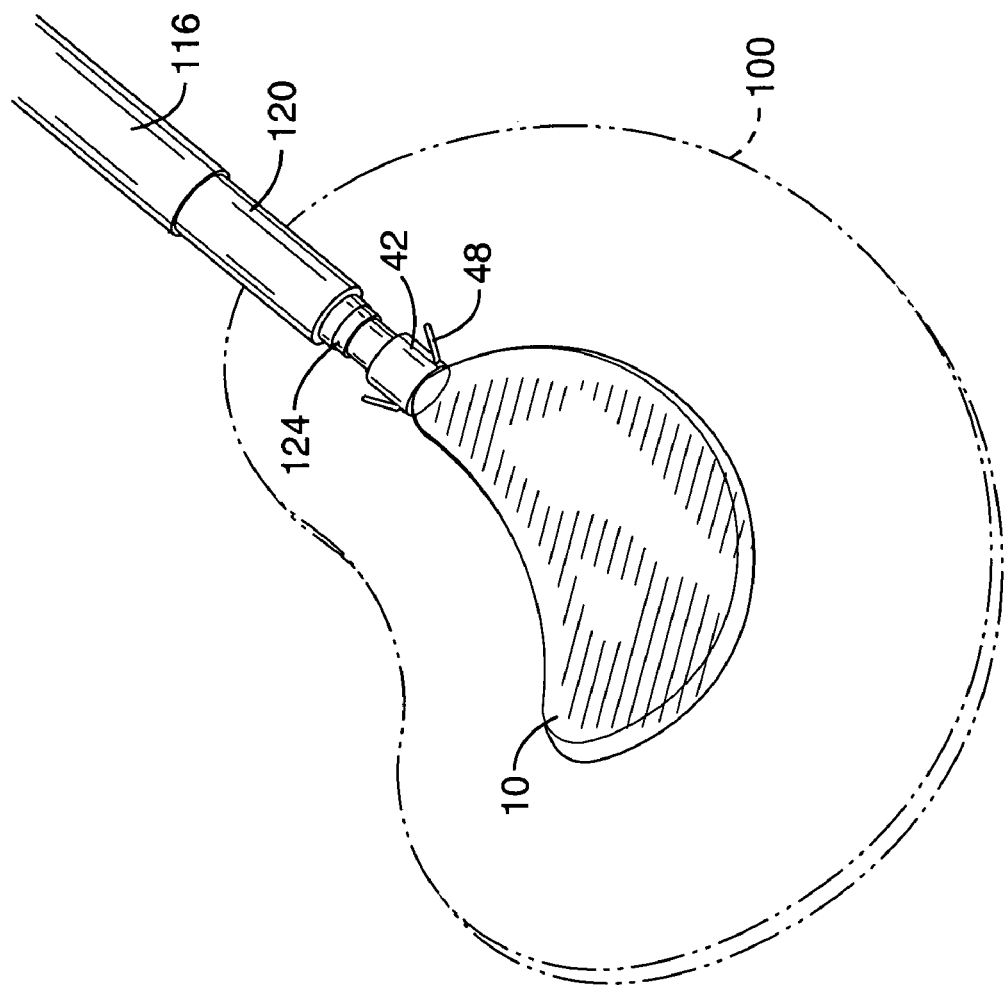
FIG. 24 is a detail view of the implant end portion of the assembly of FIG. 23.

As can be seen from FIG. 17 and FIG. 18, implant 10 can then be advanced into the nuclear space 102 by pushing launcher sheath 116 through introducer sheath 108 until handle 118 contacts handle 110. Note that the flexibility of launcher sheath 106 allows it to deflect if necessary to fit the contour of the nuclear space. FIG. 19 and FIG. 20 then show the implant being deployed by retracting both the introducer sheath 108 and the launcher sheath 116 by pulling handles 110 and 118 back toward handle 122 on fill tube 120 until they are in contact with handle 122. From FIG. 20 it can be seen that pins 48 will then spring outward into the nuclear space and into a position that is ready for engagement with the annulus. Then, as can be seen in FIG. 21 and FIG. 22, pulling back on fill tube 120 will cause the pins 48 on buttress 42 to engage the annulus 68. With inner annular buttress 42 secured in place, implant 10 can then be filled as shown in FIG. 23 and FIG. 24. Once implant 10 is filled, fill tube 120 can be unscrewed from buttress 42 and removed.

Although the description above contains many specificities, these should not be construed as limiting the scope of the invention but as merely providing illustrations of some of the presently preferred embodiments of this invention. Those skilled in the art will appreciate that other materials, structures, components, and configurations can be employed without departing from the invention. For example, collagen could be used instead of polymer, and polylysine or type 2 collagen with a cross-linking agent could be used instead of hydrogel. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Elastomer Properties

| Material | Description | Supplier | Modulus (psi) | Modulus (MPa) | Tensile strength (psi) | Tensile Strength (MPa) | Elongation (%) |
| --- | --- | --- | --- | --- | --- | --- | --- |
| Inner Annulus | | | | 5 to 10 | | 1 to 3 | 10 to 20 |
| HT-3 | aliphatic polycarbonate polyurethane | Apex Medical | 295.00 | 2.03 | 5300.00 | 36.54 | 470.00 |
| HT-4 | aliphatic polycarbonate polyurethane | Apex Medical | 990.00 | 6.83 | 7100.00 | 48.95 | 375.00 |
| HT-6 | polycarpralactone copolyester polyurethane | Apex Medical | 290.00 | 2.00 | 5800.00 | 39.99 | 850.00 |
| HT-7 | aromatic polyester polyurethane | Apex Medical | 340.00 | 2.34 | 9000.00 | 62.06 | 550.00 |
| HT-8 | aliphatic polyether polyurethane | Apex Medical | 290.00 | 2.00 | 5500.00 | 37.92 | 710.00 |
| HT-9 | aromatic polyester polyurethane | Apex Medical | 550.00 | 3.79 | 7000.00 | 48.27 | 550.00 |

TABLE 2

Osmotic Pressure as a Function of Gel Formulation

| Gel Formulation | [PEG] | [HA] | [CS] | Π (MPa) |
|---|---|---|---|---|
| 1 | 3.6% | 0.11% | — | 0.011 |
| 2 | 5.0% | — | — | 0.025 |
| 3 | 5.0% | — | 0.68% | 0.028 |
| 4 | 6.0% | — | — | 0.033 |
| 5 | 7.5% | — | — | 0.052 |
| 6 | 7.5% | 2% | — | 0.080 |
| 7 | 7.5% | — | 6% | 0.130 |
| 8 | 7.5% | 3% | — | 0.155 |
| 9 | 7.5% | — | 11% | 0.220 |
| 10 | 9% | — | 13% | 0.310 |
| 11 | 10% | — | 15% | 0.332 |

The additives in formulation #8 consisted of a pre-swollen HA-PEG gel that was dried then finely cut and incorporated into a new PEG gel.

What is claimed is:

1. A method for repairing an intervertebral disc, said disc comprising an annulus that substantially surrounds a nuclear space and is located between first and second adjacent vertebrae, said annulus having a wall, said method comprising:
    inserting an inflatable implant in a collapsed configuration through a passageway formed across the annulus wall and into the nuclear space;
    wherein said inflatable implant comprises,
        an inflatable membrane,
        said membrane having an internal chamber,
        said membrane having an internal self-sealing fill valve located within the internal chamber; and
    inflating said implant within the nuclear space from the collapsed configuration to an expanded configuration that a first portion of the membrane is located adjacent the first vertebra, a second portion of the membrane located opposite the first portion is positioned adjacent the second vertebra;
    wherein said internal self-sealing fill valve comprises internal opposing walls that are disposed relative to the membrane so as to collapse as a result of a compressive load between the first and second vertebrae, and thus between the first and second membrane portions, and thereby disposed on said internal chamber.

2. A method as recited in claim 1, wherein said membrane comprises an elastomer.

3. A method as recited in claim 2, wherein said elastomer is biodegradable.

4. A method as recited in claim 2, wherein said elastomer comprises polyurethane.

5. A method as recited in claim 4, wherein said polyurethane comprises aliphatic polycarbonate polyurethane.

6. A method as recited in claim 1, wherein said implant is inflated with a hydrogel.

7. A method as recited in claim 6, wherein said hydrogel is mixed with an additive selected from the group consisting essentially of chondroitin sulfate and hyaluronic acid.

8. A method as recited in claim 6, wherein said hydrogel comprises:
    a nucleophilic "8-arm" octomer (PEG-NH$_2$, MW 20 kDa); and
    a "2-arm" amine-specific electrophilic dimer.

9. A method as recited in claim 6, wherein said hydrogel comprises cross-linkable polyethylene glycol.

10. A method as recited in claim 1, further comprising removing nucleus pulposus tissue to form said nuclear space.

11. A method as recited in claim 10, further comprising removing said nucleus pulposus tissue by performing a postero-lateral percutaneous discectomy.

12. A method as recited in claim 1, wherein said membrane and said self-sealing valve are formed as one unitary member.

* * * * *